United States Patent [19]

Haynes

[11] Patent Number: 4,920,977
[45] Date of Patent: May 1, 1990

[54] BLOOD COLLECTION ASSEMBLY WITH LANCET AND MICROCOLLECTION TUBE

[75] Inventor: John L. Haynes, Chapel Hill, N.C.

[73] Assignee: Becton, Dickinson and Company, Franklin Lakes, N.J.

[21] Appl. No.: 262,551

[22] Filed: Oct. 25, 1988

[51] Int. Cl.$^5$ .............................................. A61B 5/00
[52] U.S. Cl. .................................... 128/770; 206/571
[58] Field of Search ............. 128/314, 760, 763, 770; 604/51, 52, 115, 264, 272, 403; 206/363–366, 569, 571

[56] References Cited

U.S. PATENT DOCUMENTS

| | | | |
|---|---|---|---|
| 4,397,318 | 8/1983 | Burns | 128/763 |
| 4,469,110 | 9/1984 | Slama | 128/314 |
| 4,592,744 | 6/1986 | Jagger et al. | 128/763 |
| 4,608,997 | 9/1986 | Conway | 128/763 |
| 4,616,649 | 10/1986 | Burns | 128/314 |
| 4,620,549 | 11/1986 | Nugent | 128/763 |
| 4,654,031 | 3/1987 | Lentz | 128/763 |
| 4,755,356 | 7/1988 | Robbins et al. | 422/102 |
| 4,761,379 | 8/1988 | Williams et al. | 206/569 |
| 4,777,964 | 10/1988 | Briggs et al. | 206/569 |

*Primary Examiner*—Max Hindenburg
*Attorney, Agent, or Firm*—Robert P. Grindle

[57] ABSTRACT

A combined throw-away lancet and blood microcollection tube assembly is provided with a housing having outer dimensions for the assembly the size of a standard test tube for ease of handling and labeling, which housing incorporates a built-in lancet and blood microcollection tube. The housing includes one or more snap-open hinged covers which may be opened and closed with one hand. A further feature of the invention is provision for incorporating the used lancet in the housing for subsequent disposal to reduce contamination potential. The entire assembly may be disposed of as a single unit after use.

20 Claims, 3 Drawing Sheets

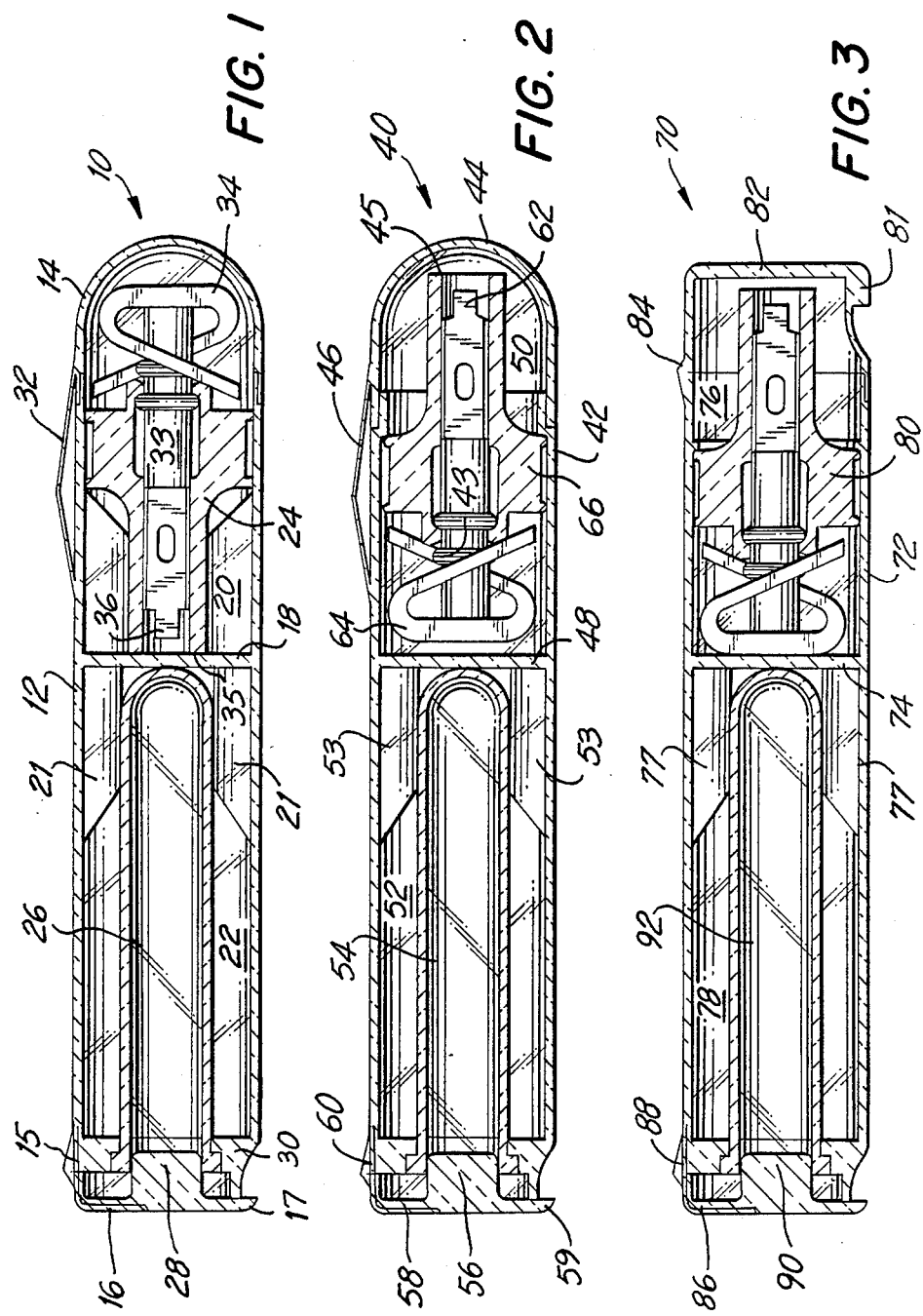

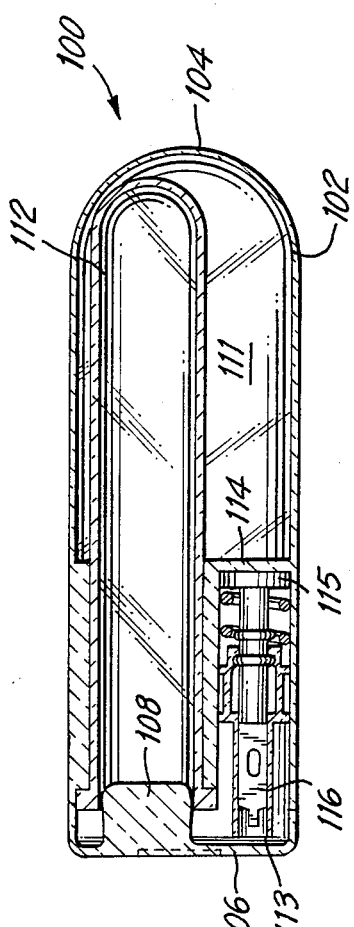
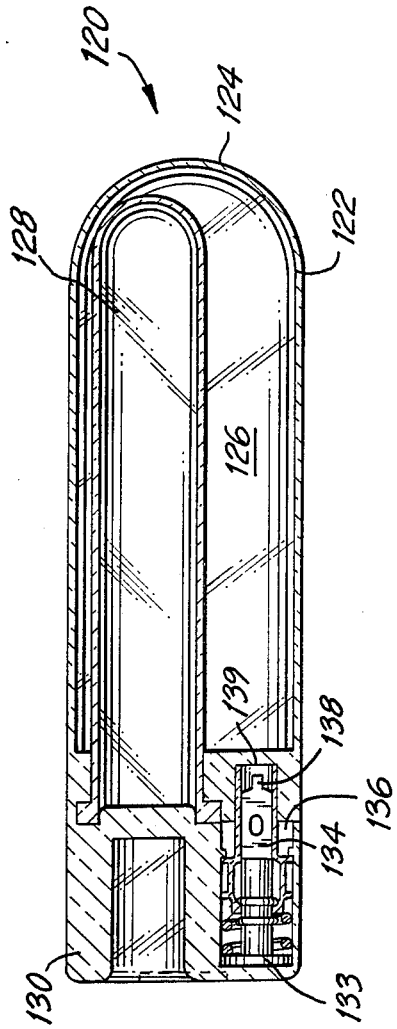
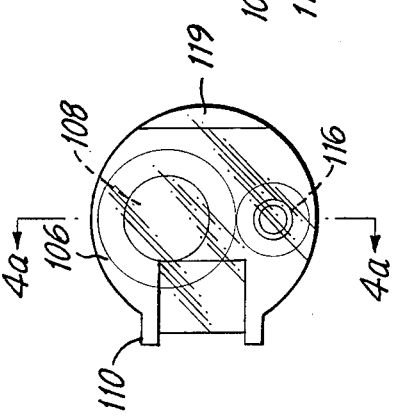
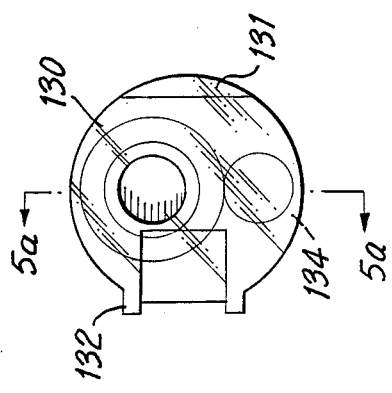

BLOOD COLLECTION ASSEMBLY WITH LANCET AND MICROCOLLECTION TUBE

BACKGROUND AND STATEMENT OF THE INVENTION

Generally speaking, this invention relates to a blood collection assembly incorporating a microcollection container together with a lancet. More particularly, this invention relates to such an assembly utilizing a housing of a dimension which makes it much easier to handle than the routine microcollection container. In addition, the assembly includes a lancet device which has a withdrawal feature so that once the blade has been inserted into the skin of a patient, the blade automatically withdraws into the lancet portion of the assembly herein. Representative lancets are described in U.S. Pat. No. 4,616,649, issued Oct. 14, 1986, which is hereby incorporated by reference in its entirety. Once skin puncture has been made, the microcollection container incorporated into the assembly of the invention is readily available for collecting blood.

In addition, the assembly of the invention includes "snap open" caps on either or both ends thereof for exposing the lancet at one end and the blood collection tube at the other end, or both the lancet and the blood microcollection tube at the one end. Both caps are integrally connected to the assembly of the invention and may be manipulated by a single hand so that user may have the other hand available for controlling or handling the patient which may be, for example, a screaming, wiggly baby. Because the caps are easily manipulated, both the blood microcollection container and the used lancet are readily closed into the assembly for protecting the user from contamination.

Practitioners in the art of assemblies of the kind to which the invention is directed are aware of the fact that analytical instrumentation makes it possible to carry out a variety of hematological or chemical diagnostic procedures on very small quantities of blood. Because of this, a patient's heel, finger or earlobe may be punctured and a very small quantity of blood collected into the microcollection container of the invention for such testing. Such arrangements obviate the need to withdraw venous blood from patients. It is this kind of situation to which the invention here is directed.

In this environment, in addition, the matter of contamination from blood samples has become a much more important factor than in the past. It is much more important to see to it that any surface contaminated by the blood sample is controlled in some manner.

With the invention claimed in this application, any difficulty engendered in taking a blood sample is further reduced dramatically by providing in the assembly itself the built in lancet for making the wound for collecting the blood sample. The lancet is positioned in the blood collector of the assembly and covered by the snap cap prior to use. This allows for sterilization of the lancet and preservation of the sterile condition prior to use. Once it is necessary to take a blood sample, the user may handle the assembly which, in its enlarged state, makes it much easier to control and open the cap and expose the lancet for taking the blood sample.

Because of the withdrawal feature of the lancet of the invention, once the wound has been made, the snap cap can be flipped back over the contaminated lancet and it is maintained in the assembly of the invention for later disposal. The technician may then simply reverse the assembly of the invention to the opposite end, in one of several embodiments, and open the snap cap for the blood microcollection container and collect a sample of blood. Again, the cap for covering the microcollection container may be manipulated by a single hand, so the technician may handle the patient with the other hand or complete other tasks which may be required during the taking of the blood sample.

Once the cap is placed back in position by manipulation with a single hand, the blood sample is in the microcollection container for subsequent examination. Once the blood sample has been examined, the entire assembly of the invention may be disposed of with the blade of the lancet firmly contained in the assembly and covered against any contamination. Moreover, the cap of the micro collection container, once the sample has been examined, may also be closed by the lab technician so that the entire assembly and any blood contained therein is self contained and easily disposed of. Thus, by the single handed capping procedure, not only is the blood collector removed from contaminating anyone coming into contact, but also in accordance with this invention the lancet is itself contained and removed from such exposure, rather than being left, inadvertently, laying near a patient.

Other advantages of the invention include, as stated above, the fact that but a single package must be made up and sterilized to achieve the entire collection procedure of a blood sample. Moreover, only this one package must be opened and handled to obtain the collection of the sample followed by proper disposal of contaminating objects.

Other objects and advantages of this invention will be apparent from the following description, the accompanying drawings and the appended claims.

DESCRIPTION OF THE DRAWINGS

FIG. 1 is a longitudinal view partially in section of a blood microcollection assembly illustrating the invention, including a sample collection container with its associated snap cap together with a self contained lancet arrangement;

FIG. 2 is a longitudinal view partially in section of a further embodiment illustrating the invention in which the lancet is positioned for use in a different manner in its separate portion of the housing of the invention;

FIG. 3 is a longitudinal view partially in section of a further embodiment illustrating the invention, and similar to the structure shown in FIG. 2, but with a different cap configuration covering the lancet portion of the housing of the invention;

FIG. 4 is a plan view of one end of another embodiment illustrating the invention, with the blood collection container and lancet utilizing a single arrangement of cap structure;

FIG. 4a is a sectional view of the device of FIG. 4 taken along lines 4a—4a thereof;

FIG. 5 is a plan view of one end of yet another embodiment illustrating the invention, and similar to that shown on FIG. 4 with the blood collection container and lancet utilizing, again, but a single arrangement of cap structure;

FIG. 5a is a sectional view of the device of FIG. 5 taken along lines 5a—5a thereof.

DETAILED DESCRIPTION OF THE INVENTION

Figures 6A, 6B, 6C, 6D, 6E:
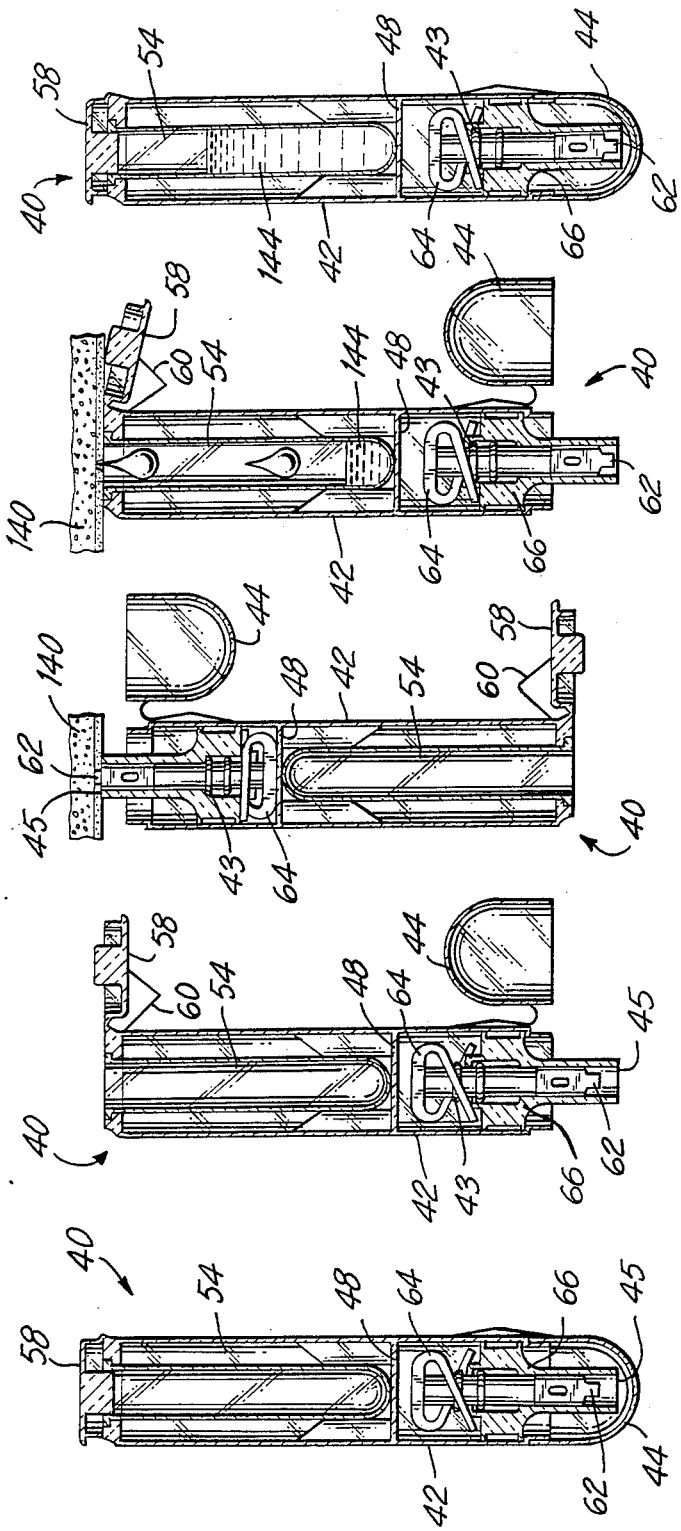
FIGS. 6a–6e show a somewhat diagramatic illustration of an operating sequence of the embodiment of the invention of FIG. 2.

Referring to the drawings in which like reference characters refer to like parts throughout the several views thereof, FIG. 1 illustrates the invention as employed in a blood collection assembly generally designated 10 having a housing 12 separated by a wall 18 into a lancet portion 20 of housing 12 and a blood collection tube portion 22 of housing 12.

As can be seen in FIG. 1, portion 22 contains a blood microcollection tube 26 supported by vanes 21 extending from wall 18 and the outer walls of the housing 12. In viewing FIG. 1, it will be seen that the dimension of the entire housing 12 is substantially larger than the conventional blood microcollection tube 26. Therefore, the user has a larger piece of material to grip while handling the problem of making a blood collection from a patient who may be alarmed at the prospect of having a skin puncture and the pain engendered from such puncture. For example, whereas a conventional blood microcollection tube is about 43 millimeters (mm) in length and about 9.6 mm in diameter, housing 12 may be the size of a conventional 10 milliliter evacuated tube which is about 100 mm in length and with about a 16 mm outer diameter.

With such an arrangement the housing of the invention may be mounted readily in a standard "test tube" centrifuge for certain laboratory test procedures. Thus, the housing of the invention may be within the range of between about 75 and 125 mm in length and within the range of between about 14 and 18 mm in diameter which eases the handling facility of the structure of the invention greatly, for the environment of blood collection from a lancet puncture. For those experienced in handling such objects, it will be apparent, furthermore, that the larger containers are much easier to label, a requirement in handling blood test samples.

Thus, the assembly 10 includes a flip-top cap 14 mounted on a strap 32 so that the user may expose the lancet 24 for making a skin puncture with the blade 36. The user, once the flip top cap 14 is opened, may remove the lancet 24 from the assembly and place the front end 35 of the lancet housing against the patient's skin. Pressing the handle 34 causes lancet body 33 to move forward and to snap past the abutment shown on body 33. This causes a rapid penetration of the patient's skin. Once this happens, the user removes pressure from operating handle 34 of the lancet 33. The spring action of handle 34 causes a withdrawal of blade 36 from the patient. When this happens, blade 36 which is now contaminated, is self contained in the housing of the lancet assembly. The lancet may then be replaced in housing 12 and cap 14 closed.

Alternatively, the user may flip open cap 16 under edge 17 for the other end 30 of assembly 12 for exposing blood microcollection container 26. Cap 16 revolves around hinge 15 and exposes the blood microcollection container for rapid collection. As can be seen in FIG. 1, cap 16 incorporates a sealing stopper portion 28 for moving into place in the top of blood microcollection container 26, once the blood has been collected. When this happens, the user may readily, with one hand, flip snap cap 16 back in place sealing microcollection container 26 until the blood sample is examined. At this point, the lancet, if it has not already been replaced, as discussed above, may be placed back into its housing portion 20 and the cap 14 therefore closed back over the lancet. Thus, the contaminated lancet and the contaminated blood microcollection container are all contained in the single assembly 12 for subsequent disposal after examination of the blood sample in blood microcollection container 26.

Referring now to FIG. 2, the assembly shows a different embodiment particularly with reference to the mounting of lancet 66. Thus, lancet 66 is positioned in its portion 50 of housing 42 with the lancet blade facing cap 44 therefore. Thus, in the assembly 40 shown in FIG. 2, the lancet is not arranged to be removed from housing 42. When the user desires to make a penetration of the patient's skin by blade 62, the user removes cap 42 which swings around on its tether 46 by a single manipulation of one hand by the user.

Then, the user places front end 45 of lancet assembly 66 against the user's skin. Because of the enlarged housing which is an aspect of the invention here, the user may readily grip the housing 42 and place the front end 45 of the lancet 66 against the patient's skin. By moving the housing 42 toward the patient, dividing wall 48 between portions 50 and 52 of housing 42 causes the wall 48 to move against the handle 64 of the lancet assembly. This causes body 66 of the lancet and abutment 33 to move forward past its associated abutment for driving blade 62 into the patient. Once this action takes place, the user merely removes the entire assembly from the patient's skin which causes the spring in the top or handle 64 of the lancet 66 to withdraw blade 62 past the front end 45 of the lancet housing. This causes blade 62 to be retracted away from any inadvertent puncture or scratch of the user's skin of the contaminated blade.

Once this has taken place, cap 44 may be rapidly moved into place and cap 58 with stopper portion 56 covering the microcollection container 54 readily snapped open by gripping edge 59 around its hinge 60 for collecting the blood sample from the puncture site. Once this has happened, cap 58 may be readily replaced single handedly to close the blood microcollection container 54. A more detailed discussion of the use of this particular embodiment of the invention is discussed below.

Referring now to FIG. 3, a further arrangement is shown similar to that of FIG. 2 except for the form of cap 82 for covering the lancet 80 portion of the entire assembly 70. Thus, the structure 72 includes a flip top form of cap 82 which may be forced open by the user's fingernail at 81 for causing cap 82 to swing around hinge 84 as opposed to the strap like arrangement 46 in FIG. 2. The rest of housing 72 is substantially the same as assembly 40 in FIG. 2 with a divider wall 74 dividing the microcollection container 92 portion 8 from the lancet portion 76, housing lancet 80. Container 92 is supported in housing 72 by vanes 77. Cap 86 is the same construction as cap 58 with a stopper portion 90 and hinge 88.

Referring now to FIG. 4 and FIG. 4a, a further embodiment 100 is shown of the invention having an assembly structure 102 defining a chamber 111. The assembly or housing 102 includes a closed end wall 104 and a single cap 106 at the open end thereof. Cap 106 includes a hinge 110 for a single-handed opening around hinge 110. In this arrangement, cap 106 includes a portion 108 for sealingly closing the blood microcollection container 112 in the assembly 100. Also, once cap 106 is opened the lancet 116 is exposed for use at the same end as the blood microcollection tube 112. Thus, the user grasps housing 102 and places the front end 113 of lancet 116 against the patient's skin and presses the assembly 102 toward the patient. This causes wall portion 114 of assembly 102 to move forward and press against top 115 of lancet body 116.

Again, as discussed previously, this action causes the cooperating abutments of lancet 116 to move past each other to force the lancet blade into the patient's skin for a rapid puncture movement. Once this happens, the user removes housing 102 from adjacent the patient's skin which causes the spring of the lancet 116 to retract the blade thereof. Then the user may simply place the front end of the blood microcollection tube 112 against the wound for collecting several drops of blood into blood microcollection container 112 for subsequent examination. Then, cap 106 may be single handedly reclosed over the entire assembly for ensuring no exposure of the blood sample until it is examined in the laboratory. Lip 119 facilitates the unsnapping of cap 106 for un covering the assembly 102 around hinge 110.

Referring to the embodiment of FIG. 5, the assembly 120 shown therein is similar to that of FIG. 4 in the sense that housing 122 is provided with a closed end 124. The open end of housing 122 provides access to both microcollection tube 128 in portion 126 and lancet assembly 134 in portion 136. However, cap 130 of assembly 120 has a larger vertical dimension, as shown, in order to accommodate lancet 134 in cap body 130 itself. Thus, the user snaps open cap 130 around hinge 132 through the facility of lip 131. When this happens, lancet 134 swings around hinge 132 with cap 130 so that the front face 139 of lancet 134 is exposed to be placed against a patient's skin.

When this positioning takes place, the user moves the entire assembly 120 including housing 122 toward the patient's skin. This serves to cause cap 130 to bear against the top 133 of lancet 134 causing the snap action of the abutments in the same manner as previously described which causes blade 138 to extend past the front surface 139 of lancet 134 and puncture the patient's skin. Immediate withdrawal of housing 122 away from the skin causes the spring action to retract blade 138 into the assembly so as to prevent exposure of the contaminated blade 138 to the user or anyone adjacent to the blade. At this point, blood may be collected by placing the front end 132 of blood microcollection container 128 adjacent the puncture.

Referring now to FIGS. 6a-6e, an operating sequence for the embodiment of blood microcollection system of FIG. 2 is shown. Thus, in FIG. 6a, and as discussed in more detail previously, assembly 40 is shown prior to use. Both closures 44 and 58 are closed ensuring sterility for the assembly prior to use. Referring now to FIG. 6b, both the lancet cover 44 is opened and the blood microcollection cap 58 is opened. This exposes front surface 45 of lancet 66. Thus, at this point in time, the user grasps housing 42 and places lancet front end 45 against the patient's skin 140 (FIG. 6C). Housing 42 is pushed forward which causes abutment 43 to move past its cooperating abutment by the wall 48 moving against top 64 of the lancet assembly.

Once the cooperating abutments move past each other, blade 62 is thrust into and penetrates the skin of a patient. Removal of the housing 42 from the skin of the patient causes the spring in the lancet 66 to retract blade 62 back past the front edge 45 thereof, which protects the patient from any further contamination. The point of puncture is shown in FIG. 6c wherein wall 48, by movement of the housing 42 in the direction of the skin 140 of the patient compresses the top and spring assembly 64 of lancet 66 to cause the puncture action.

Referring now to FIG. 6d, and as discussed previously, blade 45 is now in its retracted position and the assembly is reversed to place the front edge of blood microcollection tube 54 against the puncture in the patient's skin 140. Blood droplets 142 collect in a pool 144 at the bottom of blood microcollection container 54. Once the pool of blood 144 has been collected, as shown in FIG. 6e, cap 58 and cap 44 are closed to provide a self contained assembly 40. This assembly may then be forwarded to the lab for an analysis of blood sample 144. Once that is done, the entire assembly 40 may be discarded.

Preferably, the assembly of the invention will be comprised of a clear molded thermoplastic such as polyethylene, for example. Other materials which may be used, as will be appreciated by practitioners in the art, include various thermoplastics such as polypropylene and polyvinyl chloride. It will be understood, however, that the housing such as 42 shown in FIG. 2 as well as the blood microcollection tube 54 shown in FIG. 2 may be comprised of glass. However, glass has been found to be less desirable for certain applications because of breakage. The breakage, as will be understood by practitioners in-the art enhance the problem of contamination. The blood microcollection container itself preferably, has been properly treated to provide a hydrophilic internal surface for enhancing the flow of blood introduced therein. The internal surface of the container may also utilize a surface active agent such as a silicone coating.

With respect to the mounting of the blood microcollection tube within the assembly of the invention in the various embodiments shown, while the tube is mounted in a press fit arrangement in the support therefore, it will be understood that the blood microcollection tube could be screwed into a support therefore in the housing of the invention.

While the forms of apparatus herein described constitute preferred embodiments of the invention it is to be understood that the invention is not limited to these precise forms of apparatus, and that changes can be made therein without departing from the scope of the invention which is defined in the appended claims.

What is claimed is:

1. A self-contained blood collection assembly for developing a skin puncture and a resulting blood sample collection in a single housing comprising
    (a) an elongated housing;
    (b) said housing defining a chamber;
    (c) said chamber having a first lancet containing portion and a second blood microcollection tube portion;
    (d) said first lancet containing portion extending to a first open end;
    (e) said second blood collection tube portion extending to a second open end;
    (f) a lancet in said first lancet containing portion;
    (g) a blood microcollection tube in said second blood collection tube containing portion;
    (h) a first snap cap mounted for closing said first open end;
    (i) said first snap cap connected to said elongated housing;
    (j) a second snap cap mounted for closing said second open end; and (k) said second snap cap connected to said elongated housing.
2. The assembly of claim 1, wherein
(a) said lancet is mounted in said first lancet containing portion with said lancet facing said first open end.
3. The assembly of claim 2, wherein
(a) said first snap cap is connected to said housing by an integral tether.
4. The assembly of claim 2 wherein
(a) said first snap cap is connected to said housing by a hinge.
5. The assembly of claim 3, wherein
(a) said second snap cap is connected to said housing by a hinge.
6. The assembly of claim 1, wherein
(a) said elongated housing is within the range of between about 75 and 125 millimeters long and within the range of between about 14 and 18 millimeters in diameter.
7. The assembly of claim 1, wherein
(a) said housing is transparent.
8. The assembly of claim 1, wherein
(a) said chamber includes a wall dividing said chamber into said first lancet containing portion and said second blood microcollection tube portion.
9. The assembly of claim 1, wherein
(a) said lancet is spring loaded.
10. A self contained blood collection assembly for developing a skin puncture and a resulting blood sample collection in a single housing, comprising
(a) an elongated housing;
(b) said housing defining a chamber;
(c) said chamber having a first lancet containing portion, and a second blood microcollection tube portion;
(d) said housing having at least one open end thereof;
(e) a lancet in said first lancet containing portion, said lancet extending to said at least one opening;
(f) a blood microcollection tube in said second blood microcollection tube portion;
(g) said blood microcollection tube having a closed end and an open end;
(h) said blood microcollection tube open end positioned adjacent said at least one open end;
(i) a snap cap mounted for closing said at least one open end; and
(j) said snap cap connected to said elongated housing.
11. The assembly of claim 10 wherein
(a) said lancet has a blade; and
(b) said lancet is mounted so that said blade extends toward said at least one opening.
12. The assembly of claim 11, wherein
(a) said snap cap is connected to said housing by a hinge.
13. The assembly of claim 10, wherein
(a) said snap-cap has an enlarged body;
(b) said enlarged body includes a lancet receiving chamber;
(c) said snap cap is mounted on said housing to move from a closed position to an open position; and
(d) said lancet mounted in said lancet receiving chamber to extend into said first lancet containing portion of said housing when said snap cap is in said closed position.
14. The assembly of claim 13, wherein
(a) said snap-cap is connected to said body by a hinge.
15. The assembly of claim 10, wherein
(a) said housing is open at both ends;
(b) said first lancet containing portion extending to a first opening;
(c) said second blood microcollection tube portion extending to a second opening;
(d) a first snap cap mounted on said housing for closing said first opening; and
(e) a second snap cap mounted on said housing for closing said second opening.
16. The assembly of claim 15, wherein
(a) said first snap cap is connected to said housing by an integral tether; and
(b) said second snap cap is connected to said housing by a hinge.
17. The assembly of claim 15, wherein
(a) said first and second snap caps are connected to said housing by a hinge.
18. The assembly of claim 10, wherein
(a) said housing is transparent.
19. The assembly of claim 10, wherein
(a) said chamber includes a wall dividing said chamber into said first lancet containing portion and said second blood microcollection tube portion.
20. The assembly of claim 10, wherein
(a) said lancet is spring loaded.

* * * * *